United States Patent [19]

McCoy

[11] 3,948,741

[45] Apr. 6, 1976

[54] LIQUID PHASE CHLORINATION OF NORMAL PARAFFINS

[75] Inventor: David R. McCoy, Wappingers Falls, N.Y.

[73] Assignee: Texaco Inc., New York, N.Y.

[22] Filed: Nov. 25, 1974

[21] Appl. No.: 526,869

[52] U.S. Cl. ............................ 204/163 R; 260/660
[51] Int. Cl.² ...................................... C07C 17/10
[58] Field of Search ................ 204/163 R; 260/660

[56] References Cited
UNITED STATES PATENTS

| | | | |
|---|---|---|---|
| 3,639,494 | 2/1972 | Crocker | 204/163 R |
| 3,654,107 | 4/1972 | Lindwall et al. | 204/163 R |
| 3,864,410 | 2/1975 | Selwitz | 204/163 R |
| 3,896,183 | 7/1975 | Henderson et al. | 260/660 |

FOREIGN PATENTS OR APPLICATIONS

| | | | |
|---|---|---|---|
| 1,161,826 | 8/1969 | United Kingdom | 260/660 |
| 1,162,238 | 8/1969 | United Kingdom | 260/660 |
| 1,164,022 | 9/1969 | United Kingdom | 260/660 |

*Primary Examiner*—Leland A. Sebastian
*Attorney, Agent, or Firm*—T. H. Whaley; C. G. Ries; Carl G. Seutter

[57] ABSTRACT

Selective chemical processing of normal paraffin hydrocarbons may be carried out with increased selectivity by reacting a normal paraffin hydrocarbon reactant, in the presence of inert solvents, in a free radical (e.g., photochemically) initiated reaction.

20 Claims, No Drawings

LIQUID PHASE CHLORINATION OF NORMAL PARAFFINS

FIELD OF THE INVENTION

This invention relates to hydrocarbon conversion. More specifically, it relates to photochemically initiated processes characterized by high selectivity.

BACKGROUND OF THE INVENTION

As is well known to those skilled in the art, hydrocarbons may be converted to hydrocarbon derivatives containing functional groups (typified by halogen groups); and these may serve as a starting point for the preparation of further derivatives.

Terminally substituted alkanes (especially those with 8–18 carbons) derived from n-paraffins are valuable chemical intermediates in the production of fatty acids, amines, alcohols, esters, and sulfonates for use as detergents, fabric softeners, lubricant additives, plasticizers, etc. (F. Asinger, *Paraffins: Chemistry and Technology*, transl. B. J. Hazzard, Pergamon Press, Oxford, 1968, pp. 735–6). By contrast, secondary substituted paraffins derived from these same paraffins generally decompose to form olefins or are unreactive when attempts are made to transform them into alcohols, sulfonates, etc. (Asinger, p. 736; H. Krauch and W. Kunz, *Organic Name Reactions*, John Wiley, New York, 1964, p. 444; Jack Hine, *Physical Organic Chemistry*, McGraw-Hill, New York, 1962, Chapt. 6).

The treatment of n-paraffins, under a variety of reaction conditions to introduce, e.g., chlorine, always gives rise to a mixture of 1-chloroalkanes and secondary chloroalkanes. Although there are physical methods (U.S. Pat. No. 3,426,086) for separating the two classes of compounds from one another, and chemical means of separation are feasible utilizing the different orders of reactivity for these compounds (for example, see Chem. Abstr. 62 11671, 1965; D. J. Hurley et al., I. & E.C. Prod. Res. & Devel. 4 44, 1965), no attempts have been made to isolate the 1-chloroalkanes from such chlorination mixtures for use as chemical intermediates because the 1-chloroisomer is formed in very low selectivities. For example, chlorination of n-dodecane using a variety of chlorinating agents and reaction conditions gives only 11–13 percent selectivity of the monochloro product to 1-chlorododecane (G. A. Russell article in *Free Radicals*, Vol. 1, J. K. Kochi, ed., John Wiley, New York, 1973).

The effect of solvents in directing chlorination to a particular position in an alkane (i.e., affecting the relative reactivities of primary, secondary, and tertiary H's in the molecule has been extensively reviewed [F. asinger, Paraffins; G. A. Russell article; J. P. Soumillion, Indust. Chim. Belge, 35 1071, 1970; and B. Fell and Li-Hoan Kung, Chem. Ber. 98 2871, 1965[). No solvent mentioned in the literature to date has been found to increase the selectivity of chlorination to the terminal position of an n-paraffin (i.e., increase the reactivity of a primary H vs. a secondary H). However, aromatic solvents and other special solvents containing electron-donating groups (sulfides, amines, etc.) have been shown to drastically decrease the amount of 1-chloroalkane formed. The only chlorinated hydrocarbons investigated in the literature are $CCl_4$ and trichloroethylene. These were stated (see G. A. Russell) to have no effect on the position of chlorination in a paraffin. Soumillion states that $CCl_4$ is "inert" as far as affecting position of chlorination, and Asinger (p. 761) even states that $CCl_4$ "has not the slightest effect on the relative reaction velocities of the various types of hydrogen atoms in paraffinic hydrocarbons".

It is an object of this invention to provide a novel process for selective conversion of hydrocarbons. Other objects will be apparent to those skilled in the art.

STATEMENT OF THE INVENTION

In accordance with certain of its aspects, the method of this invention may comprise forming a charge mixture consisting essentially of liquid phase and containing (i) a normal paraffin hydrocarbon and (ii) a diluent-solvent selected from the group consisting of chlorinated aliphatic hydrocarbons, fluorinated aliphatic hydrocarbons, and chlorinated fluorinated aliphatic hydrocarbons;

chlorinating said normal paraffin hydrocarbon in the presence of a free radical initiator, thereby forming reaction mixture containing a 1-chloro normal alkane; and recovering said reaction mixture containing said 1-chloro normal alkane.

DESCRIPTION OF THE INVENTION

The charge which may be treated by the process of this invention may include compounds possessing a chlorinatable hydrocarbon moiety. The charge may preferably contain a hydrocarbon moiety (which may bear inert substituents). In the preferred embodiment the charge may be a hydrocarbon which preferably contains a primary hydrogen (i.e., a hydrogen atom on a carbon atom which latter is bonded to only one other carbon atom). Preferably, the charge is free of tertiary hydrogen atoms. More preferably, the carbon atoms in the hydrocarbon charge are all primary and secondary, i.e., the preferred hydrocarbon charge contains a normal paraffin moiety; in the most preferred embodiment it contains a normal paraffin or alkane hydrocarbon.

The hydrocarbon charge which may be advantageously treated by the process of this invention may possess a hydrocarbon chain length of 6–22 carbon atoms, more typically about 10–16 carbon atoms — these latter being of substantial economic interest.

Illustrative of the charge n-paraffins which may be treated by the process of this invention may be the following:

n-hexane
n-heptane
n-octane
n-nonane
n-decane
n-undecane
n-dodecane
n-tridecane
n-tetradecane
n-pentadecane
n-hexadecane
n-heptadecane
n-octadecane
n-nonadecane
n-eicosane
n-heneicosane
n-docosane, etc.

The charge may consist essentially of one component; or, more typically, it may contain a mixture of components. It may be identified, e.g., as a $C_{10}$–$C_{14}$ fraction, a $C_{12}$ cut, a $C_6$–$C_{22}$ fraction, a virgin atmospheric gas oil, etc.

The preferred charge hydrocarbons may be those which are in liquid phase at the temperature of operation, i.e., which are above their melting point and below their boiling point or, alternatively, which are in solution in the other components of the reaction mixture.

The most preferred of these normal paraffin hydrocarbons may be those which consist essentially of a straight carbon chain with no substituents, i.e., normal paraffins. The preferred normal paraffins may be those having 6–22 carbon atoms, say 10–16 carbon atoms. In commercial practice, the charge may preferably be a mixture containing a wide range of such components.

In practice of the process of this invention, there is formed a charge mixture consisting essentially of liquid phase and containing (i) a normal paraffin hydrocarbon and (ii) at least one diluent-solvent selected from the group consisting of chlorinated hydrocarbons, fluorinated hydrocarbons, and chlorinated fluorinated hydrocarbons. The diluent-solvents which may be employed typically may be in liquid phase at the temperature of operation and may preferably be liquids with which the hydrocarbon is at least partially miscible and more preferably completely miscible at the conditions of operation.

Although it is not necessary that the diluent-solvent be inert under the conditions of operaton, it is preferred that it be so. If the diluent-solvent is active rather than inert, it may react with, e.g., the chlorine and thus consume some of the latter at conditions less favorable for the desired reaction. It may be noted, however, that the diluent-solvent might, for example, be derived from the charge hydrocarbon or solvent. For example, if the charge solvent were 1,2-dichloroethane, it may be found that such a solvent may be converted in part during hydrocarbon chlorination to 1,1,1,2-tetrachloroethane; and this could serve as a diluent-solvent in this or in subsequent chlorination. Desirable diluent-solvents may be recovered, pure or in mixtures, from polychlorinated charge hydrocarbons.

In the preferred embodiment, however, the diluent-solvent may possess enough chlorine or fluorine moieties to render it substantially inert, i.e., toward further chlorination at the conditions of reaction. The preferred diluent-solvent may include hydrocarbons wherein at least about 30 percent of the hydrogen atoms have been replaced by chlorine or fluorine. Among the preferred diluent-solvents may be perfluorinated or perchlorinated (or perfluor-perchloro) alkanes including normal and branched-chain alkanes.

Expressed alternatively, the preferred diluent-solvent may be one which contains at least about 70 weight percent halogen; and it will typically contain at least about two and preferably at least about three halogen atoms.

The diluent-solvent may include inert substituents. Certain substituents, which are inert as above defined, may in fact increase the selectivity of reaction. These include hydroxy, nitrile, carboxylic acid, carboxylic acid ester, and ketone functionalities. It has been found that aromatic rings, sulfides, nitro-groups, amines, and phosphines when present as substituents in the diluent-solvent (used alone) may cause a decrease in desired selectivity; and accordingly it is preferred not to use diluent-solvents alone which contain these moieties.

Typical of the diluent-solvents which may be employed in practice of the process of this invention may be the following:
carbon tetrachloride
chloroform
trifluoracetic acid
trichloracetic acid
1,1,1-trichloroethane
2,2,2-trichloroethanol
trichlorofluoromethane
hexachloroacetone
trichloroacetonitrile
pentachloroethylene
ethyl heptafluorobutyrate
ethyl trifluoroacetate
methylene dichloride
1,2-dichloroethane
1,1,2-trichloro-1,2,2-trifluoroethane
1,2,3,4-tetrachlorobutane
octachloropropane
heptachloroisobutanes (mixed isomers)
1,1-dichloro-1,1,2,2-tetrafluorethane
1,1,2-trichloroethane
hexachloroethane Although it may be possible to operate with one diluent-solvent, it may be found to be desirable to utilize more than one diluent-solvent. For example, although improved results may be achieved by the use along of either carbon tetrachloride or trichloracetic acid, it is found that additional improvement (in terms of th degree of desired selectivity toward production of, e.g., terminally chlorinated paraffins) may be achieved when these two are used together.

It is possible, for example, to utilize a normally solid haloalkane (such as hexachloroethane) together with a solvent therefor (such as, e.g., methylene dichloride).

When two or more diluent-solvents are employed, it may be desirable to utilize a pair, each of which is a different species, e.g., a perhalogenated hydrocarbon (such as carbon tetrachloride) and a perhalogenated acid (such as trifluoracetic acid) or a perhaloacetone (such as hexachloroacetone).

When one diluent-solvent is employed, preferred materials may include carbon tetrachloride, chloroform, trichloracetic acid, and trifluoracetic acid. When two diluent-solvents are employed, preferred pairs may include (i) carbon tetrachloride-trifluoracetic acid, (ii) carbon tetrachloride-hexachloroethane, etc.

The amount of diluent-solvent present in the reaction mixture is preferably above about 65 volume percent and typically about 91 volume percent to, e.g., 97 volume percent. When the diluent-solvent is carbon tetrachloride, it is found that it should preferably be maintained at or above a level of 91 volume percent. Operation in these ranges (i.e., above about 91 volume percent with carbon tetrachloride and above about 65 volume percent with other diluent-solvents) permits ready attainment of selectivity of about 15 percent or greater.

In the case of carbon tetrachloride, the preferred minimum volume percentage of 91 percent may correspond to a preferred minimum volumetric ratio (volume of carbon tetrachloride per volume of hydrocarbon) of about a little greater than 10 and to a preferred minimum weight ratio (weight of carbon tetrachloride per weight of hydrocarbon) of greater than about 15. It is under these conditions in the preferred embodiment that unexpectedly high terminal selectivities may be attained.

Reaction may be carried out at temperatures adequate to maintain the bulk of the reaction mixture in liquid phase. The typical temperature employed may fall in the range minus 20°C. to about 100°C., more typically 20°–80°C., say 40°C. In practice, the temperature of operation will be above the freezing point of the reaction mass; and generally it may not be desirable to operate above the atmospheric boiling temperature of the reacton mixture (although the reaction may be carried out under pressure to raise this limit if desired). Temperature above about 100°C. tends to decrease the desired selectivity and, accordingly, such temperature may not be desirable.

Although it may be possible to use chlorinating agents typified by sodium hypochlorite, hypochlorous acid, t-butyl hypochlorite or various N-chloramines, it is found that the most preferred is chlorine. In the preferred embodiment, chlorine gas is bubbled into the reaction mixture. In other embodiments it may be desirable to add the chlorine in solution in diluent-solvent or, alternatively, to add the chlorine simultaneously to the reaction mixture with the charge hydrocarbon. Thus, preferably the reaction mixture contains only the normal paraffin charge, the diluent-solvent(s), the chlorinating agent, the free radial initiator, and reaction products. The chlorine is added in amount of 0.1–0.5, typically 0.2–0.3, say 0.25, moles per mole of charge hydrocarbon.

During the reaction, the reaction is initiated by use of a free radical initiation system such as by addition of a peroxy compound (e.g., benzoyl peroxide or ditertiary butyl peroxide) or by a thermal initiation. More preferably, the reaction mixture is subjected to the presence of electromagnetic radiation having a wave length of 1000–7000 angstrom units. It is preferred, however, that photochemical chlorination be carried out using electromagnetic radiation of about 2900–7000 angstrom units. This range embraces the visible spectrum having a wave length of about 4000–7000 angstrom units and the ultraviolet spectrum having wave lengths less than about 4000 angstrom units and down to 1000–2900 angstrom units.

In a preferred embodiment, the spectrum may include the ultraviolet and the visible ranges, viz., about 2900 to about 7000 angstrom units. It is found, however, that visible light (4000–7000 angstrom units) typically provides results which are substantially better than those obtained with ultraviolet radiation. Accordingly, the most preferred source of electromagnetic radiation is that obtained by the use of visible light having a wave length of about 4000–7000 angstrom units.

Reaction may typically be carried out in a reaction system (batch or continuous) equipped inter alia with means for agitation, temperature control, and for light control. During the reaction, it may be found that the heat liberated can be removed by heat exchange. The by-product hydrogen chloride may be withdrawn. It is preferred that the reaction be carried out under substantially anhydrous conditions; and the reactants may be dried prior to use.

During the reaction, the chlorination may be found to be extremely selective. In the chlorination of a normal paraffin such as n-dodecane it may be found that conversion of 5–80 percent, preferably 20–40 percent, say about 30 percent, may be achieved, and operation in this range minimizes polychlorination. (Conversion is defined as the weight percent of charge hydrocarbon consumed during the reaction.) The terminal selectivity (defined as the weight percent of the desired terminally monochlorinated isomer in the total monochlorinated isomers) may be a function of the diluent-solvent and is preferably above 15 % and up to about 30 percent. Control runs, carried out in similar manner but not using the process of this invention, may typically give selectivities of typically about 10–11 percent.

The desired product may be readily recovered from the reaction mixture. Preferably, the reaction mixture may, in one embodiment, be distilled to separate desired product from solvents, unreacted charge, by-products, etc. In another embodiment, the reaction mixture may be water-washed to remove unreacted chlorine, by-product hydrogen chloride, any water-soluble components, if present, dried and distilled. In still another embodiment, the reaction mixture may be stripped, as with nitrogen gas, and then distilled to separate the components. Other techniques will be apparent to those skilled in the art.

DESCRIPTION OF SPECIFIC EMBODIMENTS

Practice of the process of this invention may be apparent to those skilled in the art from the following examples wherein all parts are parts by weight unless otherwise stated.

EXAMPLE I

In this example which represents practice of the process of this invention, an agitated solution containing 10 grams of n-dodecane may be mixed with 700 ml of carbon tetrachloride at 40°C. This corresponds to a weight ratio of diluent-solvent to hydrocarbon of 105. The mixture may be irradiated with a standard 100-watt light bulb (emitting light in the visible spectrum and having a wave length of about 2900–7000 angstrom units — including some ultraviolet radiation) for 20 minutes as 0.48 equivalents (based on charge n-dodecane) of dry chlorine gas is admitted.

At the end of 20 minutes, the flow of chlorine gas is stopped, solvent carbon tetrachloride is distilled off, and the product mixture analyzed by gas chromatographic analysis. Conversion is 29 percent and terminal selectivity (percent of 1-chloro-n-dodecane in the monochlorodecane fraction) is 21.8 percent.

EXAMPLE II

In this control run, the technique of Example I was duplicated except that no diluent-solvent (carbon tetrachloride) is present. Terminal selectivity was undesirably found to be only 10.8 percent at 41.8 percent conversion.

EXAMPLE III

In this control run, the technique of Example II was duplicated. Terminal selectivity was undesirably found to be only 11.1 percent at 21 percent conversion. Thus, practice of the novel process of this invention (Example I) gives terminal selectivity almost twice as great as that of this control example.

EXAMPLE IV

In this experimental example, 32.5 grams of n-dodecane and 700 ml of carbon tetrachloride (weight ratio of 34.3) were placed in an ultraviolet photoreactor equipped with a 90-watt medium pressure arc tube which emitted electromagnetic radiation having a wave length primarily in the band 1850–3700 angstrom units. The agitated solution was maintained at 0°C. as 0.11 equivalents of dry chlorine gas (based upon charge dodecane) were admitted over 15 minutes. Analysis of the reaction mixture indicated a 20.1 percent terminal selectivity.

EXAMPLE V

In this control example, the process of Example IV was duplicated except that no diluent-solvent (carbon tetrachloride) is present. Analysis indicated a terminal selectivity of 10.6 percent.

Comparison of Examples IV and V reveals that practice of this invention will essentially double the terminal selectivity over that achieved by the control process.

EXAMPLE VI

In this experimental example, 0.028 moles of dry chlorine were absorbed in 700 ml of carbon tetrachloride at room temperature, 20°C. This solution was added dropwise over a 20-minute period to a reaction vessel containing 10 grams of n-dodecane (weight ratio is 111). The reaction vessel was irradiated with a 100-watt visible light source emitting electromagnetic radiation of wave length falling in the range 4000–7000 angstrom units. Gas chromatographic analysis of the product revealed a terminal selectivity of 24.1 percent at 14.8 percent conversion.

EXAMPLES VII – XXVI

In this series of runs, the procedure of Example I was followed except that the solvent was that listed in the table which follows. The number in parentheses represents the quantity (in milliliters) of solvent. Freon 11 is trichlorofluoromethane. Freon 113 is 1,1,2-trichloro, trifluoroethane.

| Example | Grams Dodecane | Diluent-Solvent | Temp. (°C.) | Terminal Selectivity |
|---|---|---|---|---|
| VII | 10.0 | $CCl_4$ (70) | 40–41 | 15.6 |
| VIII | 10.0 | $CCl_4$ (700) | −13 to −19 | 28.2 |
| IX | 10.0 | $CHCl_3$ (70) | 40–43 | 18.9 |
| X | 10.0 | $CHCl_3$ (60) | 50–53 | 16.5 |
| XI | 5.0 | $CCl_3CO_2H$ (37) | 49–60 | 17.6 |
| XII | 2.5 | $CF_2ClCCl_2F$ (70.3) | 0 | 20.3 |
| XIII | 5.0 | $CCl_3CH_2OH$ (20) | 40–41 | 18.7 |
| XIV | 2.5 | $CF_3CO_2H$ (15) | 40–43 | 12.7 |
| XV | 0.5 | Freon 11 (35) | 24 | 20.7 |
| XVI | 0.5 | $CCl_3CHCl_2$ (35) | 40–42 | 30.0 |
| XVII | 2.0 | $CCl_3CN$ (14) | 40–42 | 16.7 |
| XVIII | 0.5 | $CF_3CO_2E+$ (35) | 39–40 | 20.6 |
| XIX | 0.5 | $CH_2Cl_2$ (35) | 40 | 16.2 |
| XX | 2.0 | $CCl_3C(O)CCl_3$ (14) | 40–41 | 17.6 |
| XXI | 2.0 | $(ClCH_2CHCl)_2$ (14) | 39–40 | 21.7 |
| XXII | 0.5 | $CCl_2FCF_3$ (35) | −10 to −12 | 20.8 |
| XXIII | 0.5 | Freon 113 (70) | 24–25 | 30.5 |
| XXIV | 2.0 | Heptachloroisobutanes (14) | 40 | 22.5 |
| XXV | 2.0 | Octachloropropane (14) | 90–92 | 16.4 |
| XXVI | 2.0 | $(ClCH_2CHCl)_2$ (14) | 70 | 24.0 |

EXAMPLES XXVII – XXVIII

In experimental Examples XXVII – XXVIII, the procedure of Example I was followed except that two diluent-solvents are employed.

|  | Example XXVII | Example XXVIII |
|---|---|---|
| Dodecane (grams) | 2.5 | 2.5 |
| Diluent-Solvent (ml) | $CCl_4$ (150) | $CCl_4$ (165) |
| Second Diluent-Solvent (ml) | $CCl_3CO_2H$ (30) | $CCl_3CCl_3$ (15) |
| Temperature (°C.) | 9–10 | 0 to −3 |
| Terminal Selectivity | 28.3 | 27.3 |

EXAMPLES XXIX – XXXII

Results comparable to those achieved with Example I may be achieved by the use of the following illustrative diluent-solvents:

| Example | Diluent-Solvent |
|---|---|
| XXIX | 1,1,1-trichloroethane |
| XXX | ethyl heptafluorobutyrate |
| XXXI | 1,2-dichloroethane |
| XXXII | 1,1,2-trichlorthane |

EXAMPLE XXXIII

In this control run (carried out according to Example VI of U.S. Pat. No. 2,956,084) 100 parts of 5 angstrom Linde 5A molecular sieve were saturated with chlorine gas. To this solid were added 60 parts of n-dodecane (in a roundbottom glass flask); and enough carbon tetrachloride (48 parts) was added to just cover the sieves. The contents of the flask were exposed to a source of actinic light; and the flask was fitted with a thermometer and reflux condenser.

Reaction conditions of Example VI of U.S. Pat. No. 2,956,084 were adhered to. Analysis of the chlorinated product indicated a terminal position selectivity of 13.8 percent. (The selectivity for chlorination is actually lower than this because the presence of the sieves conduced selective dehydrohalogenation of non-terminal chloroparaffins.)

It is apparent that this control reaction gives a terminal selectivity substantially lower than is achieved by practice of the instant invention — g.v. Example I wherein liquid phase operation gives a 21.8 percent terminal selectivity. This represents an improvement of 158 percent.

EXAMPLE XXXIV

In this control run (carried out according to the procedure of the example immediately preceding except as indicated hereinafter) a mixture of 60 parts of n-dodecane and 48 parts of carbon tetrachloride were irradiated with light as one equivalent of chlorine gas was introduced at 30°–76°C. over 20 minutes.

Analysis of the product showed a terminal position selectivity of only 11.5 percent.

EXAMPLES XXXV – XXXIX

In this series of runs, n-dodecane was chlorinated, with 0.5 moles of chlorine per mole of n-dodecane, in the presence of visible light at 40°C. The chlorination was carried out in the presence of carbon tetrachloride in volume percent as noted in the table which follows; and the percent terminal selectivity was determined.

| Example | Vol. % $CCl_4$ in liquid mix | Vol. Ratio $CCl_4$: n-dodecane | Wt. Ratio $CCl_4$: n-dodecane | Terminal Selectivity |
|---|---|---|---|---|
| XXXV | 0 | 0 | 0 | 11.5% |
| XXXVI | 67 | 2 | 4.3 | 11.8 |
| XXXVII | 91 | 10 | 21.3 | 16 |
| XXXVIII | 98 | 49 | 104 | 21 |
| XXXIX | 99 | 99 | 211 | 23 |

From the above table it is clear that, in the absence of diluent (Example XXXV) or in the presence of a slight amount (Example XXXVI) corresponding to 67 percent of the liquid reaction mixture, the terminal selectivity is undesirably low, e.g., 11.5 percent and 11.8 percent. As the amount of diluent increases to, e.g., 91 volume percent (weight ratio of 20), the terminal selectivity unexpectedly increases to about 16 percent; and as the content of carbon tetrachloride increases further, the terminal selectivity increases to 23 percent in this series of runs.

It will be apparent to those skilled in the art that the use of reaction systems containing greater than 65 volume percent of diluent-solvent (as a percent of the hydrocarbon plus diluent-solvent) — or greater than 91 volume percent when the diluent-solvent is carbon tetrachloride — permits attainment of terminal selectivity to 1-chloro normal alkanes of greater than about 15 percent, and in stated examples as high as 30.5 percent.

The attainment of this increased selectivity is achieved typically by the use of diluent-solvent in amount of greater than about 65 volume percent typically up to about 98 volume percent, preferably 65–80 percent, corresponding to a volumetric ratio (diluent-solvent:hydrocarbon) of about 2–50 or a weight ratio of about 4–100. In the case of carbon tetrachloride, the diluent-solvent may be present in amount greater than about 91 volume percent and up to about 98 volume percent, preferably 91–95 percent, corresponding to a volumetric ratio of about greater than about 10 up to 50 or a weight ratio of greater than about 20 up to 100.

Although this invention has been illustrated by reference to specific embodiments, it will be apparent to those skilled in the art that various changes and modifications may be made which clearly fall within the scope of this invention.

We claim:
1. The method which comprises
   forming a charge mixture consisting essentially of liquid phase and containing (i) a normal paraffin hydrocarbon and (ii) a diluent-solvent selected from the group consisting of chlorinated aliphatic hydrocarbons, fluorinated aliphatic hydrocarbons, and chlorinated fluorinated aliphatic hydrocarbons, said diluent-solvent being present in said charge mixture in amount above about 65 volume percent;
   chlorinating said normal paraffin hydrocarbon in said charge mixture in the presence of a free radical initiator, thereby forming reaction mixture containing a 1-chloro normal alkane; and
   recovering said reaction mixture containing said 1-chloro normal alkane.
2. The method claimed in claim 1 wherein said diluent-solvent is present in the charge mixture in amount of about 65–98 volume percent.
3. The method claimed in claim 1 wherein said diluent-solvent is carbon tetrachloride present in the charge mixture in amount above about 91 volume percent.
4. The method claimed in claim 1 wherein said diluent-solvent is an aliphatic hydrocarbon containing at least about 70 weight percent halogen.
5. The method claimed in claim 1 wherein said diluent-solvent is an aliphatic hydrocarbon containing at least about two halogen atoms.
6. The method claimed in claim 1 wherein said photochemical chlorination is carried out in the presence of electromagnetic radiation of wave length 1000–7000 angstrom units.
7. The method claimed in claim 2 wherein said photochemical chlorination is carried out in the presence of electromagnetic radiation of wave length 2900–7000 angstrom units.
8. The method claimed in claim 2 wherein said photochemical chlorination is carried out in the presence of electromagnetic radiation of wave length 4000–7000 angstrom units.
9. The method claimed in claim 1 wherein said photochemical chlorination is carried out in the presence of electromagnetic radiation in the visible spectrum.
10. The method claimed in claim 1 wherein said paraffin is a normal paraffin containing at least one hydrocarbon having 8–18 carbon atoms.
11. The method claimed in claim 1 wherein said photochemical chlorination is carried out at temperature of about −20°C. to 100°C.
12. The method claimed in claim 1 wherein said photochemical chlorination is effected with chlorine.
13. The method claimed in claim 1 wherein said diluent-solvent includes an at least partially chlorinated or fluorinated alkane.
14. The method claimed in claim 1 wherein said diluent-solvent includes an at least partially chlorinated or fluorinated $C_1$ to $C_{10}$ alkane.
15. The method claimed in claim 1 wherein said diluent-solvent includes a perchloroalkane or a perfluoroalkane or a perfluoro-chloroalkane.
16. The method claimed in claim 1 wherein said diluent-solvent includes a perfluorinated or perchlorinated aliphatic hydrocarbon containing at least one hydroxy, nitrile, carboxylic acid, carboxylic acid ester, or ketone substituent.

17. The method claimed in claim 1 wherein said diluent-solvent includes a diluent-solvent selected from the group consisting of:
carbon tetrachloride
chloroform
trifluoracetic acid
trichloracetic acid
1,1,1-trichloroethane
2,2,2-trichloroethanol
trichlorofluoromethane
hexachloroacetone
trichloroacetonitrile
pentachloroethane
ethyl heptafluorobutyrate
ethyl trifluoroacetate
dichloromethane
1,2-dichloroethane
1,1,2-trichloro-1,2,2-trifluoroethane
1,2,3,4-tetrachlorobutane
octachloropropane
heptachloroisobutane
1,2-dichloro-1,2,2;2-tetrafluoroethane
1,1,2,-trichloroethane; and
hexachloroethane.

18. The method which comprises
photochemically chlorinating a normal $C_8$ to $C_{18}$ paraffin hydrocarbon, in the presence of visible light, in liquid phase with chlorine in the presence of, as diluent-solvent, a perchlorinated lower alkane, thereby forming a reaction mixture containing a 1-chloroalkane having 8–18 carbon atoms; and
recovering said reaction mixture containing said 1-chloroalkane having 8–18 carbon atoms.

19. The method which comprises
forming a charge mixture consisting essentially of liquid phase and containing (i) a normal paraffin hydrocarbon having 8–18 carbon atoms and (ii) at least one diluent-solvent selected from the group consisting of chlorinated aliphatic hydrocarbons, fluorinated aliphatic hydrocarbons, and chlorinated fluorinated aliphatic hydrocarbons, said diluent-solvent being present in amount of at least about 65 volume percent of said charge mixture;
chlorinating said normal paraffin hydrocarbon in said sharge mixture in the presence of electromagnetic radiation of wave length of 2900–7000 angstrom units at temperature of $-20°C$. to $100°C$., thereby forming a reaction mixture containing a 1-chloro normal alkane; and
recovering said reaction mixture containing said 1-chloro normal alkane.

20. The method which comprises
forming a charge mixture containing (i) a normal paraffin hydrocarbon having 8–18 carbon atoms and (ii) carbon tetrachloride in amount of at least about 91 volume percent of the total of said hydrocarbon and said carbon tetrachloride;
chlorinating said normal paraffin hydrocarbon in said charge mixture in the presence of electromagnetic radiation of wave length of 2900–7000 angstrom units at temperature of $-20°C$. to $100°C$., thereby forming a reaction mixture containing a 1-chloro normal alkane; and
recovering said reaction mixture containing said 1-chloro normal alkane.

* * * * *